United States Patent [19]

Sander

[11] Patent Number: 5,496,261
[45] Date of Patent: Mar. 5, 1996

[54] COMBINATION OF A VIEWING AND/OR DOCUMENTING APPARATUS AND AN ENDOSCOPE AS WELL AS A METHOD OF OPERATING THE COMBINATION

[75] Inventor: Ulrich Sander, Oberkochen, Germany

[73] Assignee: Carl-Zeiss-Stiftung, Heidenheim, Germany

[21] Appl. No.: 283,791

[22] Filed: Aug. 1, 1994

[30] Foreign Application Priority Data

Jul. 30, 1993 [DE] Germany .......................... 43 25 577.9

[51] Int. Cl.$^6$ .............................. A61B 1/00; G02B 21/00
[52] U.S. Cl. .......................... 600/163; 600/112; 600/102; 359/379; 359/383
[58] Field of Search .................................. 600/102, 111, 600/112, 137, 166, 173, 163, 174; 354/62; 348/65; 359/368, 379, 380, 383, 384, 377

[56] References Cited

U.S. PATENT DOCUMENTS 2,705,490  4/1955  Littmann ................................ 359/379
4,448,498  5/1984  Muller et al. ........................... 359/379
5,282,085  1/1994  Volkert et al. ......................... 359/377

FOREIGN PATENT DOCUMENTS

9003458 U  7/1990  Germany .
4116810   11/1992  Germany .
2255651   11/1992  United Kingdom .

Primary Examiner—Richard J. Apley
Assistant Examiner—John P. Leubecker
Attorney, Agent, or Firm—Walter Ottesen

[57] ABSTRACT

The invention is directed to a combination of a viewing and/or documenting apparatus and an endoscope connected forward thereof. The endoscope can be pulled out relative to the apparatus and can be deflected at an angle if desired. A coupling is provided between the focusing position of the main objective of the apparatus and the pull-out length of the endoscope in such a manner that the intermediate image supplied by the endoscope is always focused independently of the particular pull-out length.

16 Claims, 5 Drawing Sheets

COMBINATION OF A VIEWING AND/OR DOCUMENTING APPARATUS AND AN ENDOSCOPE AS WELL AS A METHOD OF OPERATING THE COMBINATION

FIELD OF THE INVENTION

The invention relates to the combination of a viewing and/or documenting apparatus and an endoscope connected forward of the apparatus. The endoscope is mounted so as to be movable relative to the apparatus. The invention also relates to a method of operating the combination.

BACKGROUND OF THE INVENTION

In the area of minimal invasive surgery, a viewing and/or documenting apparatus with an endoscope is an advantageous combination of different medical therapeutic and/or diagnostic instruments. A combination of this kind is already disclosed in German patent publication 4,116,810. Here the suggestion is made to place an endoscope forward of a viewing and/or documenting apparatus configured as a surgical microscope. A scissors-like linkage member is mounted between the objective of the surgical microscope and the ocular of the endoscope. The endoscope is linearly movable along a rigid guide column attached to the surgical microscope; that is, the endoscope is mounted so that it can be pulled away.

However, several disadvantages result when utilizing the arrangement according to German patent publication 4,116,810. The scissors-like linkage member takes up a considerable amount of space to accommodate its movement and therefore significantly affects the surgeon. In addition, it is necessary that the surgeon refocus the intermediate image supplied by the endoscope after changing the pull-out length of the endoscope which disturbs the work sequence during surgery. Finally, a change in viewing angle is only possible with the aid of an arrangement of this kind in that the surgical microscope, which is mounted on a stand, can be pivoted completely.

Similar problems also develop when, in lieu of the surgical microscope as the viewing and/or documenting apparatus, an adapter is provided having electro-optical image recorders mounted therein.

SUMMARY OF THE INVENTION

It is an object of the invention to provide a combination of a viewing and/or documenting apparatus and an endoscope connected forward thereof. It is also an object of the invention to provide a method of operating the combination which offers the surgeon a high degree of comfort and affects the surgeon as little as possible with respect to space in which to move for performing surgery.

The combination of the invention combines a viewing and/or documenting apparatus and an endoscope. The combination comprises the apparatus which includes a main objective having a variable focal distance; the endoscope which includes a lens system for generating an intermediate image; and, means for coupling the endoscope to the apparatus so as to permit the endoscope to be pulled away from the apparatus in a pregiven direction to any length within a pregiven range wherein the apparatus is always focused on the intermediate image irrespective of the length within the range.

The coupling of the endoscope pull-out length to the main objective of the viewing and/or documenting apparatus guarantees that for each realizable pull-out length of the endoscope, there is an automatic focusing onto the intermediate image generated by the endoscope thereby eliminating a sometimes difficult refocusing during the surgery. The main objective of the viewing and/or documenting apparatus is an objective with a variable focal distance.

As an endoscope for mounting forward of the apparatus, a stereoscopic endoscope has proven especially advantageous wherein the stereoscopic component beam paths are transmitted via a common optical system as disclosed in German patent publication 4,225,507 which corresponds to U.S. patent application Ser. No. 08/100,276, filed Aug. 2, 1993, incorporated herein by reference. The realization or recordation of a three-dimensional image is possible with the aid of a stereoscopic endoscope of this kind. The realization or recordation of such images defines an essential requirement with respect to minimal invasive surgery. The foregoing notwithstanding, a conventional monocular endoscope can also be used in the context of the invention.

Known surgical microscopes as well as adapters having electro-optical image recorders mounted therein can be used as viewing and/or documenting apparatus which can be used in combination with an endoscope in accordance with the invention.

Furthermore, it is possible according to the invention to always obtain a constant overall magnification for the viewer or for the electro-optical image recorders mounted in an adapter. This is achieved in that the pull-out length of the endoscope is used as a control variable for a magnification changer device of the viewing and/or documenting apparatus. The magnification adjustment is then controlled in dependence upon the particular pull-out length so that a constant overall magnification results. The viewer observes the interesting details of the object then always with constant overall magnification, for example, via a surgical microscope without the necessity of making a self-adjustment. The same applies for a documentation apparatus having electro-optical image recorders mounted therein.

In addition to the one-dimensional positioning of the endoscope relative to the viewing and/or documenting apparatus along one axis, it is also possible according to the invention to deflect the endoscope relative to the viewing and/or documenting apparatus via one or more articulating connections between the apparatus and the endoscope. In this way, the viewing space is significantly increased.

For this purpose, and alternatively or supplementary to the last-mentioned feature, various deflecting elements can be mounted within the combination of the invention which make a variation of the observer viewing angle possible.

With the aid of the combination of the invention incorporating the viewing and/or documenting apparatus and the endoscope of variable pull-out length, the number of necessary endoscopes of different lengths can thereby be reduced because a specific range in length is covered by a single endoscope via the variable pull-out length.

BRIEF DESCRIPTION OF THE DRAWINGS

The invention will now be described with reference to the drawings wherein:

FIG. 1b shows the embodiment of FIG. 1a with the endoscope pulled out a distance from the apparatus greater than shown in FIG. 1a;

DESCRIPTION OF THE PREFERRED EMBODIMENTS OF THE INVENTION

Figure 1A:
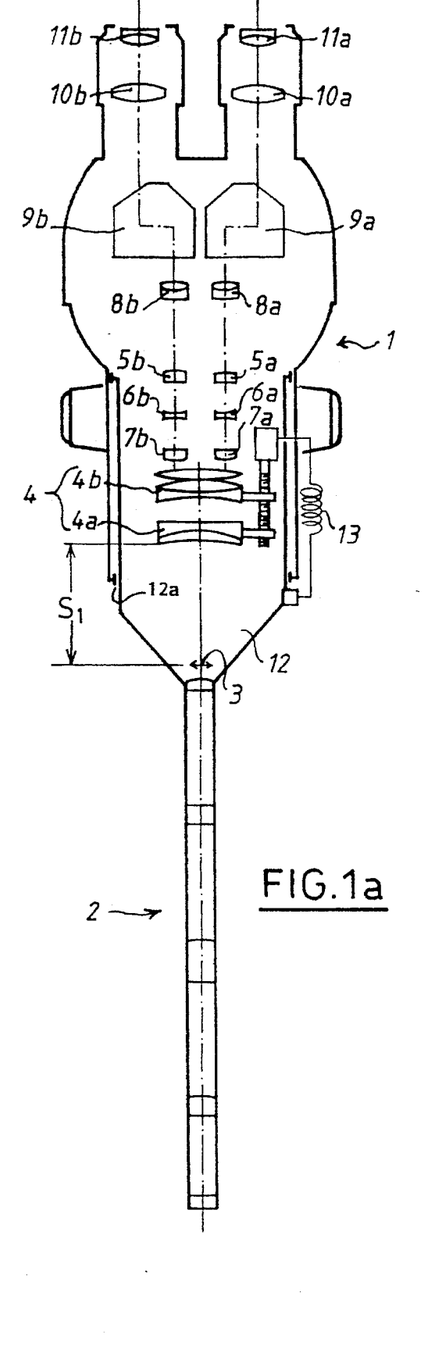
FIG. 1a is a schematic representation of a first embodiment of the combination of the invention wherein the endoscope can only be displaced linearly for different pullout lengths with the viewing and/or documentation apparatus here being in the form of a surgical microscope.
Figure 1B:
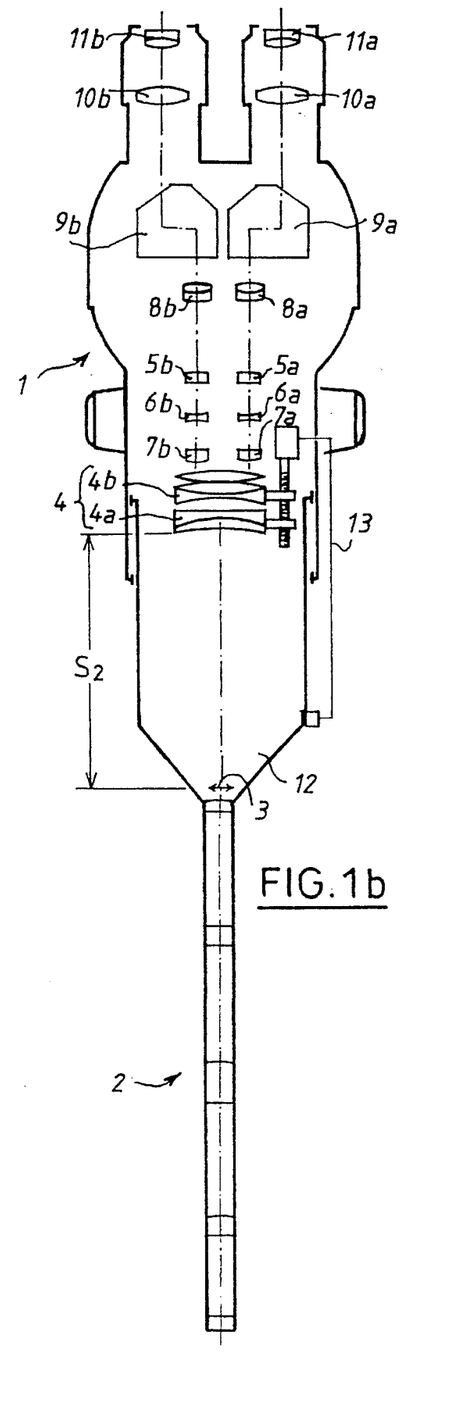

FIGS. 1a and 1b show a first embodiment of the combination of the invention wherein a surgical microscope 1 is provided as the viewing and/or documenting apparatus and wherein an endoscope 2 having a variable pull-out length is mounted forward of the apparatus. Different endoscope pull-out lengths are shown in FIGS. 1a and 1b.

The endoscope 2 used in this embodiment corresponds in the optical configuration to the endoscope which is described in German patent publication 4,225,507 which corresponds to U.S. patent application Ser. No. 08/100,276, filed Aug. 2, 1993, and incorporated herein by reference. In this application, a stereoscopic endoscope is disclosed wherein the two stereoscopic beam paths are transmitted by a common optical system. This stereoscopic endoscope has a lens system which defines mutually intertwined stereo beam paths. An intermediate image supplied by the endoscope is viewed by the observer with the surgical microscope. The intermediate image contains all stereo data and so guarantees the required spatial impression for the observer.

The surgical microscope 1 includes a main objective 4 which has a variable focal distance. The main objective 4 is mounted forward of a magnification changing device (5a, 6a, 7a; 5b, 6b, 7b) for the two stereoscopic viewing beam paths. For this purpose, a known zoom system having a continuously variable magnification is utilized in the embodiment shown. A Galilei changer can be used as an alternate to the zoom system. The following are mounted downstream of the magnification changer device (5a, 6a, 7a; 5b, 6b, 7b) in the stereoscopic viewing beam paths: barrel lenses (5a, 8b), deflecting prisms (9a, 9b) as well as ocular lenses (10a, 11a; 10b, 11b).

The combination includes a surgical microscope 1 and the endoscope 2 of variable pull-out lengths connected forward of the microscope. In this combination, and depending upon the area of application, pivotable or fixedly-mounted viewing tubes can be used in order to provide the most ergonomical work position for the surgeon.

The surgical microscope 1 can further be equipped with out-coupling elements in the viewing beam paths. These elements make possible a partial outcoupling of the viewing beam paths and thereby make a documentation possible.

The common main objective 4 for both stereo-viewing beam paths has a variable focal distance as shown substantially in the surgical microscope main objective disclosed in German utility model registration G 9,003,458.9. The main objective 4 of variable focal distance is referred to in the following as a variable-focus lens and comprises several individual lens elements. These include a negative member 4a as well as a positive member 4b which are movable relative to each other so that the spacing therebetween can be varied. A focal distance variation between 150 mm and 450 mm is possible at the object side by displacing the members 4a and 4b relative to each other.

The endoscope 2 can be pulled out in one dimension and this is realized with the aid of a pull-out intermediate component 12. The endoscope 2 is rigidly mounted on the intermediate component 12 in the embodiment shown. For this purpose, an insert connection such as a bayonet connection or a threaded connection is used. The intermediate component 12 is movable linearly along guides 12a within the housing of the surgical microscope 1.

The variable pull-out length of the endoscope 2 can also be realized in ways other than shown in FIGS. 1a and 1b. Accordingly, it is, for example, possible to provide self-locking guide rails or to displace the intermediate component 12 via a thread in the housing of the surgical microscope 1.

In addition to the one-dimensional rigid connection between the apparatus (configured as a surgical microscope 1) and the intermediate component 12 or the endoscope 2, it is also possible to mount the intermediate component 12 so as to be pivotable on the particular apparatus. The surgeon can then select between the various types of usage of the combination of the invention, that is, between viewing via the surgical microscope 1 alone or with an endoscope 2 connected forward thereof.

According to the invention, the adjustment of the actual focal distance $S_1$ or the focusing position of the variable-focus lens 4 is coupled to the particular desired pull-out length of the endoscope 2. The coupling 13 is realized here in that the surgical microscope 1 is sharply focused via the variable-focus lens 4 on the intermediate image 3 supplied by the endoscope 2 for each possible pull-out length of the endoscope 2. The actual pull-out length then operates in each case as a control variable for the exact focusing of the variable-focus lens.

The coupling 13 is shown schematically in FIGS. 1a and 1b and can, for example, be configured mechanically in a first embodiment. For this purpose, a gear arrangement is provided which couples the pullout of the endoscope 2 to the displacement, relative to each other, of the lens members (4a and 4b) of the variable-focus objective 4 with an appropriate gear ratio.

Figure 5:
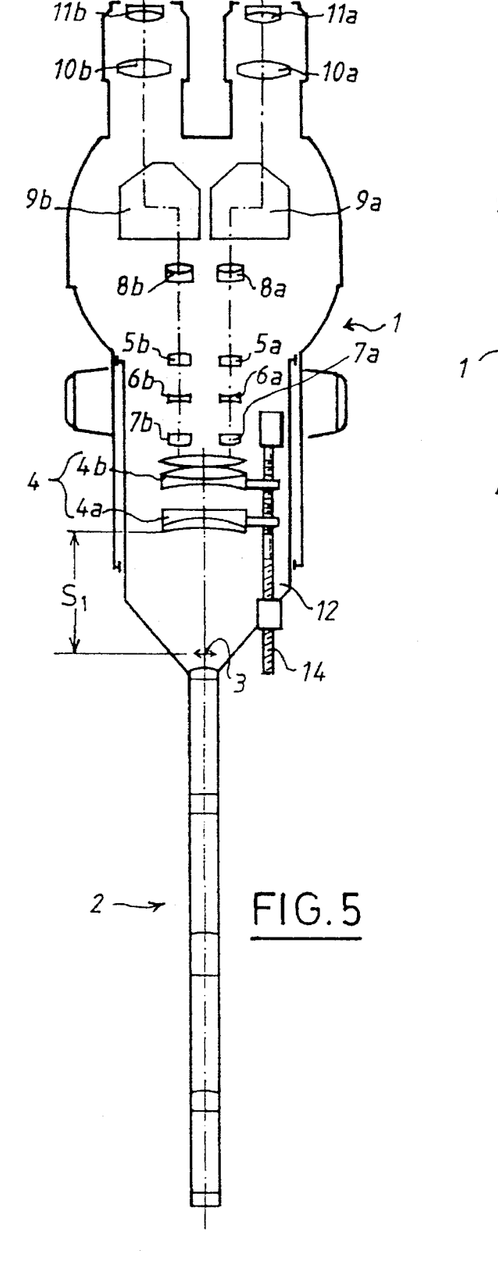
FIG. 5 is a schematic of another embodiment of the combination of the invention wherein the endoscope is coupled to the apparatus configured as a surgical microscope with the aid of a mechanical coupling; and, FIG. 6 is a schematic of still another embodiment of the combination of the invention wherein the endoscope is coupled to the apparatus configured as a surgical microscope with the aid of an electromotor coupling.

FIG. 5 shows a combination of the invention having a mechanical coupling. In the embodiment, the coupling means coupling the endoscope to the stereo microscope includes a gear assembly. When the main objective 4 is adjusted, the threaded spindle 14 rotates which, in turn, is coupled to the intermediate component 12 thereby linearly displacing the latter. The coupling can be adjusted by suitably selecting the thread pitch of the spindle 14.

Alternatively, it is possible in a second embodiment to provide an electromotor coupling via an open-loop or a closed-loop control circuit wherein the particular pull-out length of the endoscope 2 is detected by displacement transducers or encoders and an electromotor drive displaces the lens members of the variable-focus objective 4 relative to each other in such a manner that an exact focusing on the intermediate image is always present. The displacement transducer signal acts in this embodiment as a control variable for the drive of the variable-focus objective 4.

Figure 6:
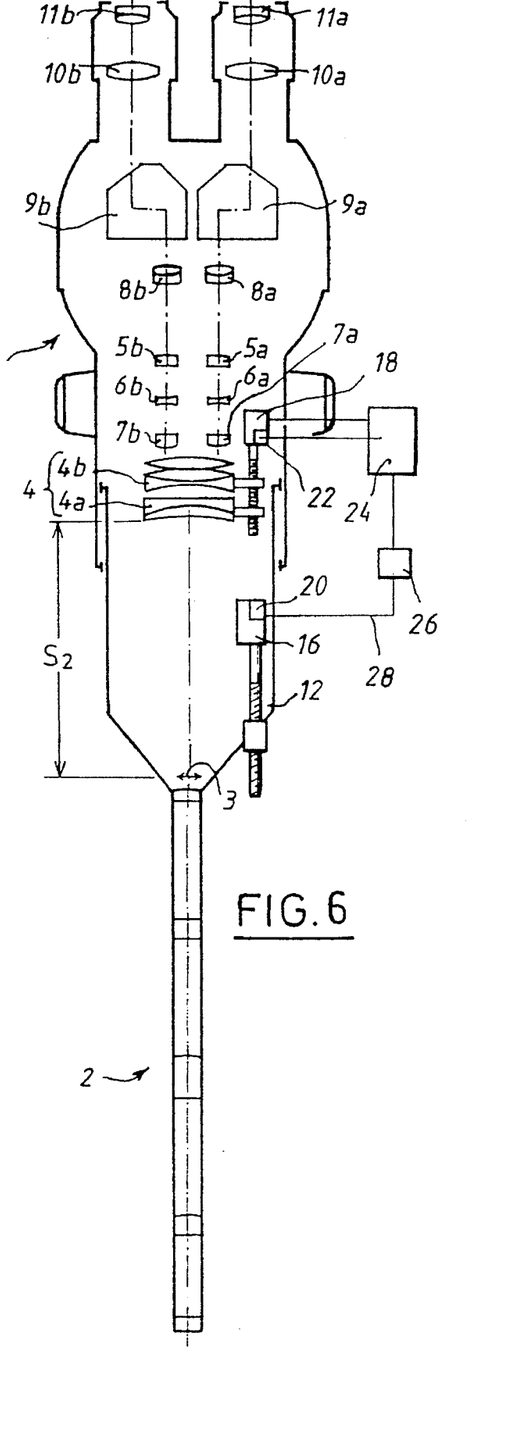

FIG. 6 shows a combination of the invention having an electromotor coupling. In this embodiment, the coupling means includes a first separate step motor 16 for adjusting the pull-out length of endoscope 2 and a second step motor 18 for displacing the elements (4a, 4b) of the objective relative to each other. Each of the step motors has an encoder (20, 22) associated therewith which detects the particular displacement. Thus, encoder 20 detects the displacement of the endoscope 2 and encoder 22 detects the displacement of elements (4a and 4b) relative to each other. A control unit 24 receives the respective signals from the encoders (20, 22) and emits a corresponding drive signal to the other step motor so that, overall, a constant total magnification results.

If required, a more complexly configured variable-focus objective can be used. It is here only essential that the particular focusing state of the variable-focus objective is coupled to the pull-out length of the endoscope.

In the method described above, the particular focusing state of the variable-focus objective 4 is automatically coupled to the pull-out length of the endoscope 2. In addition to this operation, the viewing and/or documenting apparatus and the forward endoscope 2 can, however, also be driven in the non-coupled state. First, the automated coupling of the endoscope pull-out length and the focusing state is deactivated via a coupling operator-controlled element such as switch 26 connected into the line 28 as shown in FIG. 6. Thereafter, for a fixedly adjusted pull-out length of the endoscope 2, focusing to the different object planes takes place by actuating a focusing operator-controlled element (not shown) of the variable-focus objective. The operator-actuated switch 26 opens and closes the electrical connection between control unit 24 and step motor 16 thereby switching the coupling in and out between the endoscope pull-out length and the focusing state of the variable-focus objective 4.

In FIG. 1b, the same surgical microscope 1 with the endoscope 2 is shown but with a greater pull-out length of the endoscope 2. A greater focal distance $S_1$ of the variable-focus objective 4 is automatically adjusted for this pull-out length with the aid of the coupling 13 of the invention.

A different focal distance of a variable-focus objective usually also causes a different total magnification of the viewed object detail for the viewer. For this reason, it is further possible according to the invention, to couple the magnification changer device (5a, 6a, 7a; 5b, 6b, 7b) to the variable-focus objective 4 or to the pull-out length of the endoscope 2 in such a manner that a constant total magnification for the viewer always results. For this purpose, a pancratic magnification changer system or zoom is used as a magnification changer device as shown in the embodiment of FIGS. 1a and 1b. The pancratic magnification changer system makes possible a continuous variation of the magnification. The actual pull-out length of the endoscope 2 then also operates as control variable for the particular magnification state. Here, it is also possible to configure the variable-focus objective 4 and the magnification changer device as a single optical system which, in turn, is coupled to the pull-out length of the endoscope 2.

In each of the embodiments of FIGS. 5 and 6, the coupling (mechanical or electromotoric) is so designed that the desired constant total magnification always results.

A series of further embodiments of the combination of the invention are provided in addition to the one-dimensional pullout of the endoscope in order to make a larger space for surgery accessible to the surgeon. Accordingly, the combination of the invention can be mounted on a motorized carrier system as described in German patent publication 4,202,922 which corresponds to U.S. Pat. No. 5,332,181, filed Jan. 19, 1993, incorporated herein by reference. In this way, a computer-controlled spatial positioning is possible in dependence upon application. A defined alignment of the combination is provided in combination with a motorized carrier system of this kind relative to the patient depending upon the desired viewing direction. After the spatial alignment of the endoscope relative to the patient, the suitable work position within a cavity of the body of the patient can be adjusted with the aid of the variable pull-out length.

In addition to only a one-dimensional pullout of the endoscope relative to the viewing and/or documenting apparatus, it is further possible to mount one or more articulated connections between the viewing and/or documenting apparatus and the endoscope which make a deflection of the endoscope relative to the viewing and/or documenting apparatus possible. This provides an increase of the space available for surgery or an increase in the magnification of the portion of the space for surgery as well as increased operating convenience.

Figure 2:
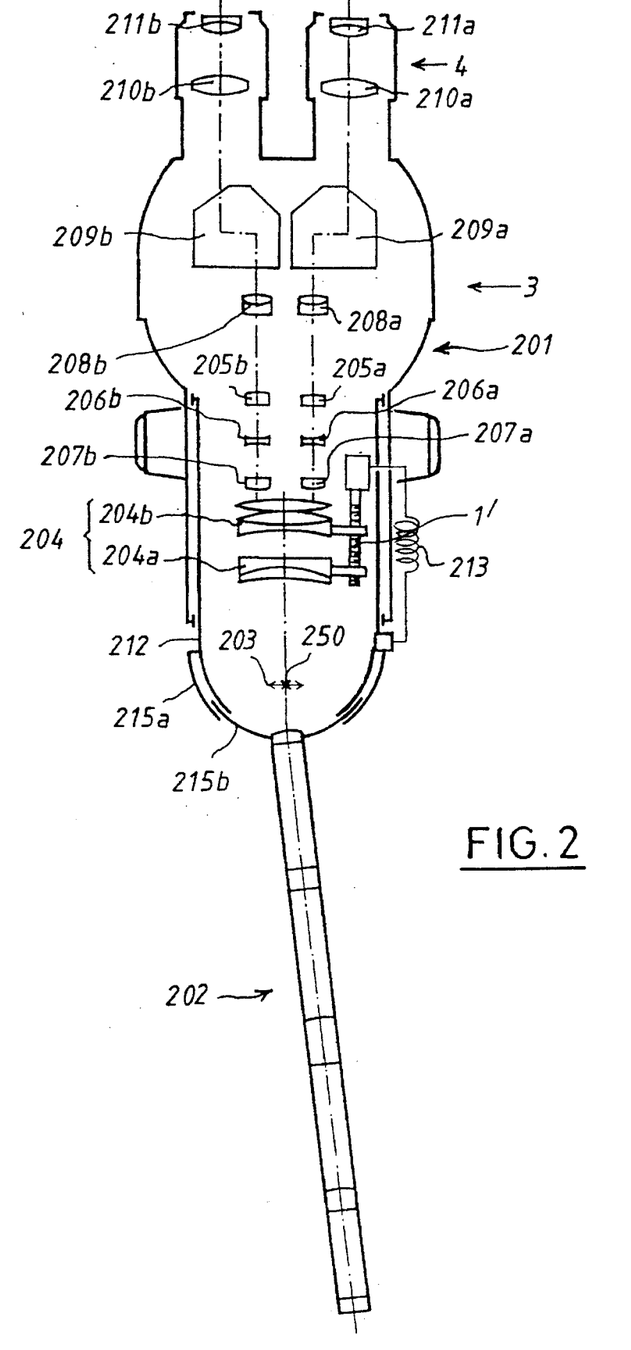
FIG. 2 shows a second embodiment of the combination of the invention wherein a swivel connection is provided between the apparatus configured as a surgical microscope and an endoscope with the swivel connection permitting the endoscope to be deflected angularly with respect to the surgical microscope.

A corresponding embodiment is shown in FIG. 2 wherein a surgical microscope is again provided as the viewing and/or documenting apparatus. The surgical microscope 201, as well as the endoscope 202, has in principle the same configuration as the embodiment of FIGS. 1a and 1b. A pull-out intermediate component 212 is again provided for connecting the surgical microscope 201 and endoscope 202. The pull-out length of the intermediate component 212 is coupled to the focusing position of the variable-focus objective 204 of the surgical microscope 201 as described above. In addition to the embodiment of FIGS. 1a and 1b, a mechanical rotation point 250 is, however, realized for the endoscope 202 in the intermediate image plane 203 of the endoscope 202. The mechanical rotation point 250 lies in the focus plane of the main objective 204 because of the coupling according to the invention. A deflecting possibility of this kind is realized by a ball and socket rotating joint (215a, 215b) in the intermediate component 212. The ball and socket rotating joint (215a, 215b) includes a guide part 215a in the intermediate component 212 and a correspondingly curved counterpiece 215b connected to the endoscope. This makes possible a pivoting of the endoscope 202 about the rotation point 250 in the intermediate image plane 203 within specific limits.

A viewing angle change of the combination of the invention to increase the viewing volume can also be realized in that at least one deflecting element is mounted in the viewing beam path of the viewing and/or documenting apparatus and/or endoscope. Here, the use of deflecting mirrors or prisms is possible. It should here be noted that, in dependence upon the number of deflecting elements used, image erecting systems must be used so that the viewer sees an upright and laterally correct image.

Figure 3:
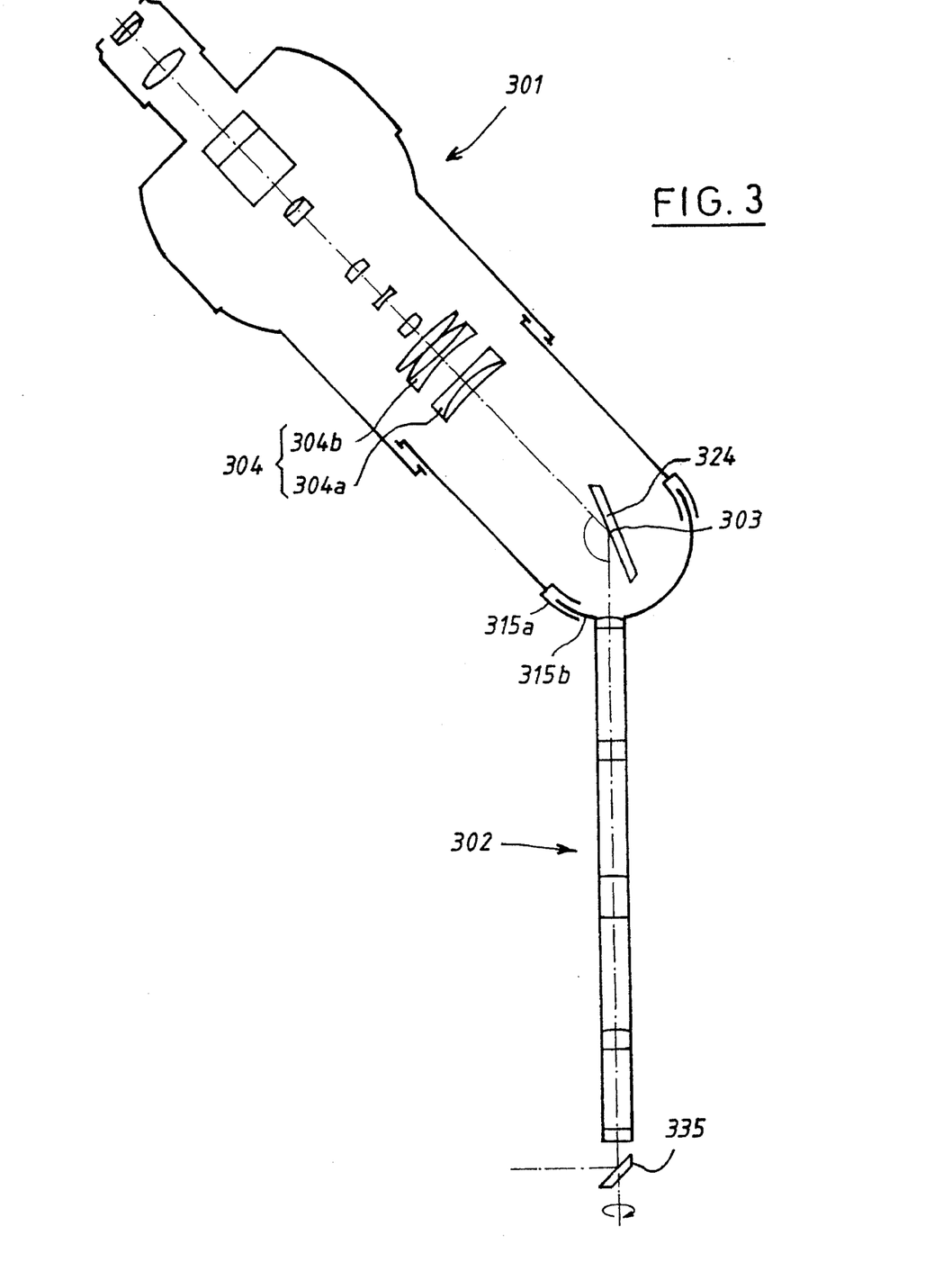
FIG. 3 is another embodiment of the combination of the invention wherein the apparatus is configured as a surgical microscope with deflecting means being interposed between the endoscope and the surgical microscope.

An embodiment of the combination of the invention and two deflecting elements is shown schematically in FIG. 3. A surgical microscope 301 again represents the viewing and/or documenting apparatus. The surgical microscope 301 again has essentially the same configuration as in the embodiments of FIGS. 1a, 1b and 2. A pull-out intermediate component 313 is provided for connecting the surgical microscope 301 and endoscope 302. The variable pull-out length of the endoscope 302 is coupled to the focusing position of the variable-focus objective 304 of the surgical microscope 301 as described above. Because of the lateral view of the surgical microscope 301, the coupling is not shown for reasons of clarity.

The endoscope 302 is mounted on the intermediate component 312 via a ball and socket rotating joint (315a, 315b) so as to be deflectable. The ball and socket rotating joint (315a, 315b) comprises, in turn, a guide part 315a and a counterpiece 315b connected to the endoscope 302 in the intermediate component 312. A substantially greater pivoting movement of the surgical microscope 301 and endoscope 302 is possible because of the additional use of the deflecting element 324 in the intermediate component, this being the case without vignetting occurring. The deflecting element 324 is pivoted about the double deflecting angle when deflecting the combination of the surgical microscope 301 and endoscope 302 in order to guarantee a correct reproduction for the viewer. A further deflecting element 335 is provided at the distal end of the endoscope. This deflecting element 335 can be rotated by the surgeon about the optical axis of the endoscope 302 and therefore make possible a variable viewing angle adjustment. The deflecting element 335 at the distal endoscope end can also be operated by a motor.

The embodiments described above for enlarging the region of surgery viewed can be combined with each other or be supplemented; that is, the possible embodiments of the combination of the invention are not limited to the exemplary combinations disclosed.

Figure 4:
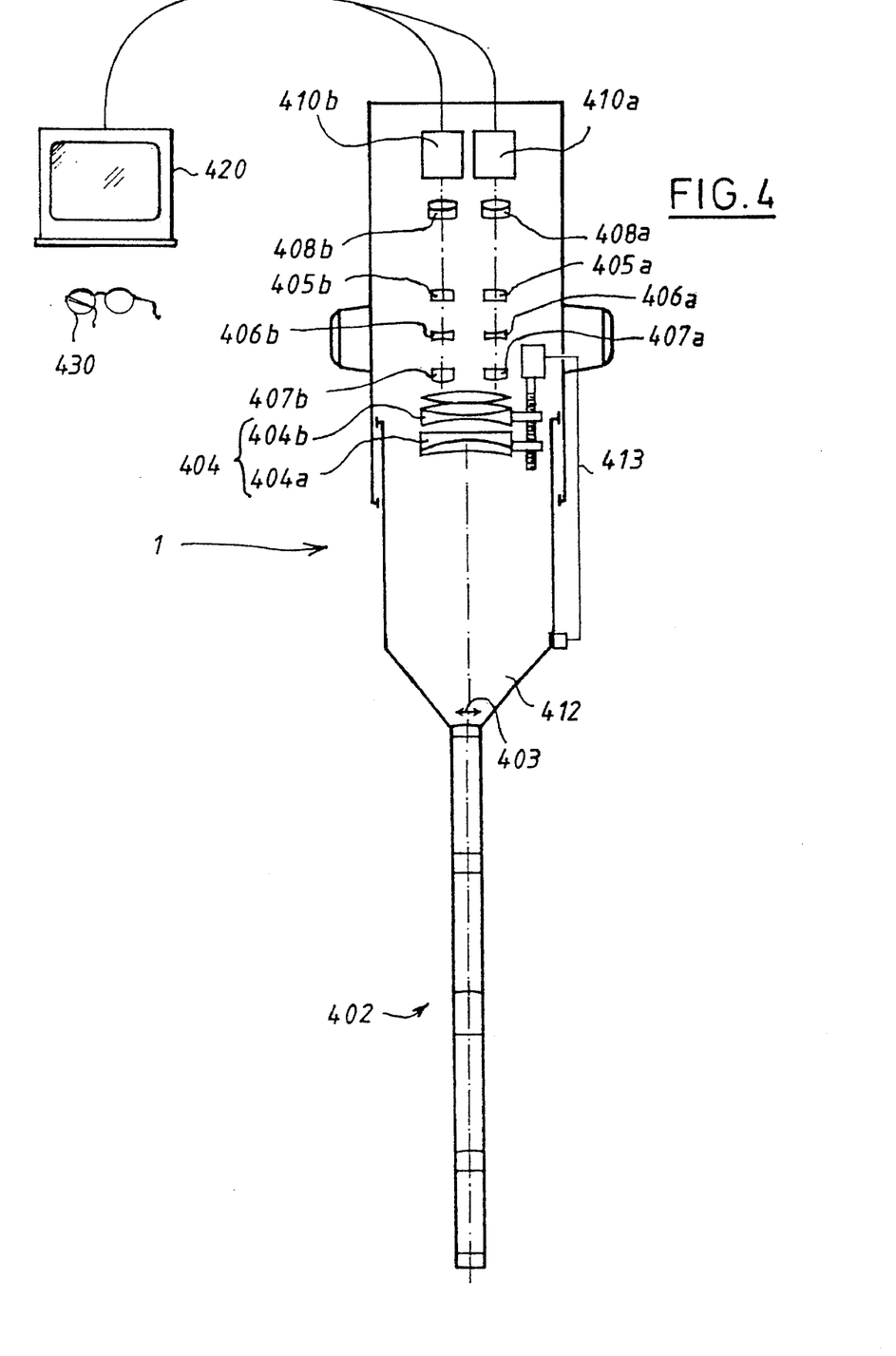
FIG. 4 is a schematic representation of a further embodiment of the combination of the invention wherein only a linear displacement of the endoscope is possible and wherein an adapter is provided as the viewing and/or documenting apparatus with the adapter incorporating electro-optical image recorders mounted therein.

A still further embodiment of the combination of the invention is shown in FIG. 4. In contrast to the embodiments described above, an adapter 401 is provided as the viewing and/or documenting apparatus. The adapter 401 is provided with electro-optical image recorders (410a, 410b) mounted therein in lieu of the binocular viewing tube. The documentation of the object viewed via the endoscope 402 is possible with the electro-optical image recorders (410a, 410b). Likewise, the display of the viewing field can take place via a suitable video monitor 420 and the viewing can take place via corresponding shutter spectacles or anaglyphic spectacles 430 during surgery.

Otherwise, the configuration with the pull-out intermediate component 412 having a pull-out length coupled to the focusing setting of the variable-focus objective 404 corresponds to the previously described embodiments.

It is understood that the foregoing description is that of the preferred embodiments of the invention and that various changes and modifications may be made thereto without departing from the spirit and scope of the invention as defined in the appended claims.

What is claimed is:

1. A combination of a viewing and/or documenting apparatus and an endoscope, the combination comprising:

said apparatus which includes a main objective having a variable focal distance;

said endoscope which includes a lens system for generating an intermediate image; and, means for coupling said endoscope to said apparatus so as to permit said endoscope to be pulled away from said apparatus in a pregiven direction to any length within a pregiven range wherein said apparatus is always focused on said intermediate image irrespective of said length within said range.

2. The combination of claim 1, said apparatus and said endoscope conjointly defining a viewing beam path; said objective having a predetermined setting when said apparatus is focused on said intermediate image; and, said combination further comprising magnification changer means mounted in said path downstream of said main objective as seen in the viewing direction; and, said coupling means being adapted so as to couple said magnification changer means to said setting of said main objective and to said length within said range so as to always provide an overall constant magnification.

3. The combination of claim 1, said coupling means comprising an intermediate component for connecting said endoscope to said apparatus.

4. The combination of claim 3, said coupling means further comprising a mechanical coupling between said intermediate component and said apparatus.

5. The combination of claim 4, said mechanical coupling being a gear assembly.

6. The combination of claim 2, said main objective and said magnification changer means conjointly defining a single optical system.

7. The combination of claim 3, said coupling means further comprising an electromotor coupling between said intermediate component and said apparatus.

8. The combination of claim 3, said coupling means further comprising a first electric motor means for displacing said intermediate component and said endoscope relative to said apparatus; second electric motor means for adjusting said main objective; sensor means for detecting the displacement of said intermediate component and for emitting a sensor signal indicative of said displacement; and, control means for driving said second motor means for adjusting said main objective in dependence upon said sensor signal.

9. The combination of claim 1, further comprising an electromotor driven carrier system for holding said combination thereon.

10. The combination of claim 8, said control means being connected to said first electric motor means; and, said combination further comprising an operator-actuated switch interposed between said control means and said first electric motor means for interrupting the connection of said first electric motor means to said control means.

11. The combination of claim 3, said intermediate component including pivot means for pivotally connecting said endoscope to said intermediate component thereby permitting said endoscope to be angularly deflected relative to said apparatus.

12. The combination of claim 11, further comprising an operator-actuable deflecting element for changing the viewing angle seen through said apparatus.

13. The combination of claim 1, said endoscope further including a lens system for defining intertwined stereo beam paths.

14. The combination of claim 1, said apparatus being a surgical microscope.

15. The combination of claim 1, said apparatus being an adapter having electro-optical image recorders mounted therein.

16. A method of operating a combination of a viewing and/or documenting apparatus and an endoscope which includes a lens system for generating an intermediate image, the method comprising the steps of:

providing said apparatus to include a main objective having a variable focal distance; and, providing a coupling for coupling said endoscope to said apparatus so as to permit said endoscope to be pulled away from said apparatus in a pregiven direction to any length within a pregiven range wherein said apparatus is always focused on said intermediate image irrespective of said length within said range.

* * * * *

UNITED STATES PATENT AND TRADEMARK OFFICE
CERTIFICATE OF CORRECTION

PATENT NO. : 5,496,261

DATED : March 5, 1996

INVENTOR(S) : Ulrich Sander

It is certified that error appears in the above-identified patent and that said Letters Patent is hereby corrected as shown below:

In column 3, line 66: delete "(5a, 8b)" and substitute -- (8a, 8b) -- therefor.

In column 5, line 53: delete "$S_1$" and substitute -- $S_2$ -- therefor.

Signed and Sealed this

Twenty-eighth Day of May, 1996

*Attest:*

BRUCE LEHMAN

*Attesting Officer*   *Commissioner of Patents and Trademarks*